United States Patent [19]

Denney

[11] 4,245,041

[45] Jan. 13, 1981

[54] TRIGLYCERIDES ASSAY AND REAGENTS THEREFOR

[75] Inventor: Jerry W. Denney, Carmel, Ind.

[73] Assignee: American Monitor Corporation, Indianapolis, Ind.

[21] Appl. No.: 858,187

[22] Filed: Dec. 7, 1977

[51] Int. Cl.³ .......................... C12Q 1/32; C12Q 1/44
[52] U.S. Cl. ........................................ 435/15; 435/19; 435/26
[58] Field of Search .......................... 195/103.5 R, 99; 435/15, 19, 26

[56] References Cited

U.S. PATENT DOCUMENTS

| | | | |
|---|---|---|---|
| 3,331,752 | 7/1967 | Struck et al. | 435/26 |
| 3,703,591 | 11/1972 | Bucolo et al. | 195/103.5 R |
| 3,915,647 | 10/1975 | Wright | 435/26 |
| 4,038,146 | 7/1977 | Nonaka et al. | 195/103.5 R |
| 4,056,442 | 11/1977 | Huang et al. | 195/99 X |

FOREIGN PATENT DOCUMENTS 50-39593  4/1975  Japan .................................. 195/103.5 R

OTHER PUBLICATIONS

Bergmeyer, *Methods of Enzymatic Analysis,* vol. 1, Academic Press, Inc., New York, 1974, pp. 136–144.
Labouheur et al., *Bull. Soc. Chim. Biol.,* 48, 747, (1966).
Boehringer Mannheim Catalog, No. 15558, p. 106, (1975).
Colowick et al., *Methods in Enzymology,* vol. 1, Academic Press, Inc., New York, 627 and 639, (1955).
*Webster's Dictionary of the English Language,* Unabridged "Encyclopedic Edition", 1131, (1977).

*Primary Examiner*—Esther M. Kepplinger
*Attorney, Agent, or Firm*—Robert A. Spray

[57] ABSTRACT

An improved triglyceride assay and reagent system which provides the introduction of iron into a reaction mixture in which glycerol from hydrolyzed triglycerides is coupled to a NAD/NADH indicator system, and measuring the resultant change of the oxidation state of the iron by use of an iron chelator, thereby improving the sensitivity and performance of the assay.

6 Claims, No Drawings

TRIGLYCERIDES ASSAY AND REAGENTS THEREFOR

I. Introduction

The present invention relates to a reagent system and assay methodology for the quantitative estimation of triglycerides in biological fluids.

Concepts of the present invention provide a new and improved reagent system for assaying for triglycerides, and the assay which utilizes these reagents.

II. High Significance of Triglycerides and Triglyceride Assays to Mankind

Triglycerides, which are triesters of fatty acids with glycerol, have very significant importance to mankind, in that they provide potent storage forms of energy in human biochemistry. About 18% of the total body weight in man is composed of adipose tissue, which in turn is comprised of about 90% (dry weight) of triglycerides; and it is the catabolism of these triglycerides which represents the major source of all body energy available to man, with the exception of glucose metabolism.

As triglycerides represent energy storage forms, they are mobilized and circulated in the bloodstream associated with protein carrier molecules known as lipoproteins.

The existence of elevated circulating levels of triglycerides (hypertriglyceridemia) in human serum has long been thought to be implicated in coronary artery disease. In fact, about 50 percent of the atheromatous lesions that occur in the coronary arteries are triglycerides.[1]

[1] Böttcher, C. J. F., Boelsa—Van Houte, E., KAAR, Romeny-Wachter, C. C., Woodford, F. P., and Van Gent, C. M., *Lancet, ii* 1162, as cited by Searcy, Ronald L., *Diagnostic Biochemistry,* 487 (McGraw-Hill, 1969).

The significant role of triglycerides in coronary artery disease, a disease which has been long recognized as the leading cause of death and of incapacitating disability and physical restriction in the United States, is shown by the hypertriglyceridemia observed in a high percentage of patients with known coronary artery disease or myocardial infarction.

It has been long recognized that dietary patterns have tremendous influence on circulating levels of triglycerides; and thus effective measurement of these levels of triglyceride would alert the medical clinician to that portion of the population that is extremely susceptible to hypertriglyceridemia, and thus point out the desirability of restrictive or modifying dietary patterns of those persons, so as to decrease the possibility or severity of coronary artery disease later in life.

In addition to being implicated in coronary artery disease, hypertriglyceridemia has also been associated with certain types of liver disease, diabetes mellitus, pancreatitis and glycogen storage disease.

The importance of a simple, sensitive, and reproducible assay for triglycerides is thus so great that it can hardly be overestimated; for at the present time large segments of an afflicted population are denied this critical assay, due to the relative paucity of facilities available to perform the known tests, due to technological difficulties.

The prior art throughout the years, accordingly, has attempted quite a variety of triglyceride assays; for the prior art in the medical field has long recognized the critical importance of triglyceride assays. These prior art attempts have been many and varied, including variations and more distinct departures from one another; however, as shown herein, the prior art procedures have all suffered from one or more disadvantages.

The present invention greatly advances the state of triglyceride assays, as well as simplifies the technique involved, thus making this important and critical preventative test available to greater segments of the population; and the higher availability of a reliable triglyceride assay, in turn, provides for many persons a healthier and fuller and longer life.

III. Prior Art, and Disadvantages Thereof

Medical science has long recognized the vital need to accurately establish a means of quantitating triglyceride levels, for the life-prolonging and life-improving uses such as mentioned above; and studies tending to confirm the implication of hypertriglyceridemia in the pathogenis of coronary artery disease have heightened this need.

Triglycerides, which are members of a general class of compounds known as lipids or fats (other major constituents of this class of compounds being phospholipids, cholesterol, and cholester esters) have had various assays proposed and attempted through the years.

III. A. Early Indirect Assays Attempted by Prior Art

The earliest attempts of numerical estimation of circulating triglycerides involved techniques which are indirect, involving measurement of the whole class of lipids, due to the technological difficulties of actual triglyceride assays. In the indirect method, the quantity of total lipids was determined gravimetrically (itself not a very accurate determination) by extracting serum with organic solvents, evaporating the solvent, and weighing the amount of lipid that was extracted. This extracted lipid would contain cholesterol and cholesterol esters, and phospholipid, in addition to the triglycerides.

The analyst would then try to determine, as best he could, by other procedures, the serum content of phospholipids, cholesterol, and cholesterol esters.

Triglyceride content would then be estimated by subtracting the thus-estimated weight of phospholipids, cholesterol, and cholesterol esters from the relatively inaccurate weight of the total lipid measured, according to the following formula:

Triglyceride=Total lipids−[phospholipids+cholesterol+1.67 cholesterol esters] where the 1.67 is a factor based on the average molecular weight of the cholesterol esters.

There were, however, major drawbacks to this indirect type of estimation of triglyceride content:

1. To get an estimation of a single component, namely triglycerides, it was necessary to perform at least 4 separate analyses with the attendant possible errors involved; the magnitude of the error in each of the assays therefore would be compounded or at least lead to indefiniteness and inaccuracy in the estimation of triglyceride content.
2. Additionally, in a normal situation, triglycerides compromise only 1/10 to 1/5 of the total lipid content; thus, as the actual triglyceride content becomes lower, the precision of the estimation becomes extremely poor, if not altogether useless or dangerously illusory.
3. The use of a factor, such as the 1.67 multiplier for cholesterol esters, was based on the assumption that the fatty acid content of the cholesterol esters remained constant between individual serums, a fact which was shown later not to be entirely true for all people.

4. Even in the estimation of total lipids, oftentimes other non-lipid type constituents would be extracted into the organic solvent, thus leading to overestimation of total lipids and consequently of the triglycerides also.

III. B. Hydrolytic Techniques of Prior Art Involving Colorimetric Determination of Glycerol Later approaches to triglyceride testing centered arount the determination of glycerol which resulted from hydrolysis or saponification of the triglyceride molecule; these are the so-called hydrolytic techniques now mentioned.

Various ones of the hydrolytic procedures, and modifications thereof, were attempted through the years. Generally, however, the hydrolytic techniques were lengthy multiple-step methods or procedures. They involved as a first step the extraction of lipids from serum with an organic solvent. The next step in those processes was to remove the phospholipids and other interfering substances from the solvent phase, for they would yield erroneous results by falsely elevating subsequent portions of the assay. After phospholipids and other potentially interfering substances were removed, the triglycerides were then subjected to either saponification under alkaline conditions or to transesterification.

The end product of both processes was the liberation of one molecule of glycerol from each molecule of triglyceride present in the system. It was the free glycerol thus liberated which would then be determined by a variety of color reactions; and then, from that glycerol determination, a direct inference would be made as to triglyceride content of the original specimen.

One of the earliest embodiments of the hydrolytic techniques was that of Blix[2], in which glycerol from triglycerides and phospholipids was reacted with hydroiodic acid to form isopropyl iodide. The resulting iodide product was then quantitated by titration, and then the amount of glycerol calculated. The obvious problem involved with this technique is that it was relatively non-specific in that phospholipids were hydrolyzed as well as triglyceride, and they were thus wrongly estimated as additional triglyceride.

[2]Blix, G.: *Biochem. Z.* 305:145, 1940.

Some several years later, Van Handel and Zilversmit[3] attempted a variation in which serum lipids were extracted with a chloroform-methanol mixture, and the phospholipids removed from the organic solvent by treatment with Doucil (a zeolite). The triglycerides remaining in the solvent were then hydrolyzed, and the liberated glycerol was oxidized to formaldehyde with periodic acid according to the procedure of Lambert and Neish[4]. The formaldehyde so formed was then reacted with chromotropic acid to form a violet chromophore which was then spectrophotometrically quantitated.

[3]Van Handel, E. and Zilversmit, D. B., *J. Lab. and Clin. Med.*, 50:152 (1957).
[4]Lambert, M. and Neish, A. O., *Can. J. Research*, 28B:83 (1950).

Carlson and Wadström[5] then attempted a hydrolytic technique, similar to that of Van Handel and Zilversmit except that silicic acid was used to remove phospholipids. In addition, an extra-extraction step was included to remove fatty acids from the organic phase.

[5]Carlson, L. A. and Wadström, *Clin. Chem. Acta.* 4:197 (1959).

This procedure, as well as hydrolytic procedures in general, was quite involved and lengthy, and required or involved essentially the following several steps: extraction of serum with methanol and chloroform; boiling; an overnight incubation; and evaporation of the chloroform extract to a volume of about 2 milliliters and subjection of the chloroform extract to silicic acid chromotography. The chloroform eluate containing the triglycerides would then be evaporated and the residue reconstituted with ethanol and potassium hydroxide, and allowed to sit at near boiling for 30 minutes in order to saponify the triglycerides present.

The mixture was then extracted with a portion of petroleum ether to remove fatty acids. Then the glycerol was extracted with sulfuric acid, and oxidized to formaldehyde with sodium periodate. The excess periodate was then destroyed by the attition of sodium arsenite, and the formaldehyde would then be reacted with chromotropic acid to give a violet chromophore which was spectrophotometrically read at a wave length of 570 namometers.

Although subsequent modifications to the above methodologies have somewhat shortened or improved these procedures, nevertheless the extreme assay length and the high degree of technological difficulty involved prevented the needed utilization of the analyses by large segments of the population. Only a few samples at a time were able to be processed, due to the burdensome requirements of glassware and laboratory apparatus, as well as the human engineering problem in maintaining sample integrity in spite of the great number of transfer steps in the methods.

Additionally, these methods required numerous labile or caustic reagents and involved the evaporation of potentially explosive organic solvents; and thus these methods represented substantial bodily-injury risk to the analyst. The extreme labor (and thus extra cost) involved in these assay techniques was of course a further disadvantage, and prevented their widespread use as a routine clinical test.

In the continuing attempt of the prior art to speed up the procedure and to reduce the degree of technological difficulty involved, Lofland[6] proposed a hydrolytic procedure for the determination of triglycerides, in which the latter portion of the assay was carried out by automated means. The serum lipids were first extracted with isopropanol, and the phospholipids removed by treatment with zeolite. The extracts were then saponified by alkali; and then the reaction of glycerol with periodate to form formaldehyde, and subsequent estimation of the formaldehyde with chromotropic acid, was done by automated means.

[6]Lofland, H. B. Jr.: *Anal. Biochem.* 9:393 (1964).

Subsequently, Kessler and Lederer[7] proposed a modification of the Lofland method, in which serum is extracted with isopropanol and the phospholipids are removed with zeolite; in this method, the subsequent saponification, oxidation to formaldehyde, and colorimetric estimation of formaldehyde, were all done by automated means. Kessler and Lederer, however, found that considerable amounts of glucose could be carried into the organic phase during the extraction process, and when subjected to periodate would give false positive reactions.

[7]Kessler, G. and Lederer, H., *Automation in Analytical Chemistry*, edited by Skeggs, L. T., New Jersey, Mediad, page 341 (1965).

To overcome this problem, the zeolite was combined with small quantities of copper sulfate and calcium hydroxide to destroy the glucose present. Additionally, the formaldehyde was estimated by reaction with a beta-diketone, and an amine, to form a lutidine-type compound which would then be estimated by fluorescence techniques.

Although this technique presented some advantages in triglyceride testing, it still suffered serious drawbacks. For example: multiple labile or caustic reagents were required; the sample still had to be extracted manually; and interfering phospholipids had to be manually removed prior to the automated portion of the assay. In addition, the automated testing equipment required considerable set-up time, and required considerable maintenance; and further, although the authors asserted good correlation with manual procedures, subsequent authors found that hypertriglyceridemic sera gave apparently falsely evaluated results when compared to the same sera run by the manual procedures.[8] These workers suggested that better correlation would be obtained by the use of unsaponified blank determinations to correct the observed test results. However, this modification would approximately double the cost of the assay, as well as slow down the rate of analysis.

[8]Claude, J. R., Corre, F., and Levallois, C.: *Clin. Chem. Acta.* 19:231 (1968).

III. C. Hydrolytic Attempts Involving Enzymatic Determination of Glycerol

Recognizing difficulties of prior art procedures, and in an attempt to gain specificity in the assay procedure, and to alleviate the use of caustic reagents, other authors[9] attempted to measure glycerol enzymatically. These procedures basically consisted of direct saponification of serum containing triglycerides with alkali in alcohol at elevated temperatures, neutralization with magnesium sulfate, and then the determination of free glycerol content in the alcoholic solution by the following reaction sequence:

[9]Eggstein, M. and Kreutz, F. H., *Klin. Wochenschr.*, Vol. 44:262 (1966).

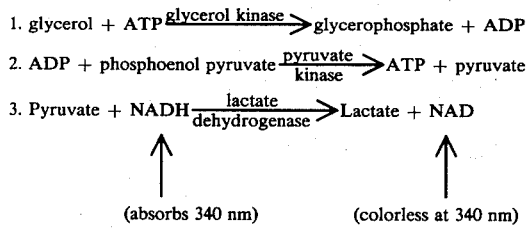

Thus, recalling that for each molecule of triglyceride one molecule of glycerol would be formed in the saponification, each molecule of glycerol would in turn run through the reaction sequence and convert one molecule of NADH to NAD with a corresponding loss of absorbance when measured at 340 nanometers in a spectrophotometer.

Although these methods yielded some advantage over the colorimetric determinations of glycerol, they still required the manual saponification process to be carried out in a separate tube from the glycerol assay. Additionally, they were time-consuming in that a blank procedure (which eliminated the presence of glycerol kinase in the reaction sequence) had to be run on each individual specimen to eliminate the effects of interfering substances on the reaction sequence such as the enzyme alkaline phosphotase on the reaction sequence. This enzyme, which is a common constituent of serum and which may vary markedly between patients, had the effect of catalyzing the conversion of ATP to ADP; and this in turn would cause the phosphoenol pyruvate to convert to pyruvate, etc., culminating in a false overestimation of glycerol.

As a further disadvantage, this blank correction factor necessitated an increase in the time necessary to accomplish the procedure as well as almost doubling the needed amount of an already expensive reagent system.

III. D. Totally Enzymatic Procedures of Prior Art

The prior art still recognized its disadvantages, and continued to propose departures and variations for assays for the determination of triglycerides. Bucolo and David sought to further simplify enzymatic determination of triglyceride by replacing the alkaline hydrolysis step used by the prior art with an enzymatic hydrolysis. These authors accomplished this by using "both a lipase and a protease".[10]

[10]Bucolo, G. and David H.: *Clin. Chem.*, 19:476 (1973), and Bucolo's U.S. Pat. No. 3,703,591.

This approach of Bucolo and David represented what might be considered not only a substantial departure but indeed a great step forward, in that for the first time the entire triglyceride assay could be carried out in a single reaction vessel, thereby greatly simplifying the assay procedure. Additionally, freedom from the potential interference of phospholipids was obtained, as the enzyme lipase proved specific for fatty acid esters of glycerol.

Despite the fact that the preferred method of Bucolo and David represented an advancement in the state of the art of triglyceride testing, it had its shortcomings also, in that as a system it required the spectrophotometric observation of NADH and its conversion to NAD and concomitant loss of optical density at 340 nanometers.

As a first problem of that method, the system measured color loss; and thus for a specimen which contained no triglycerides, one would obtain a very large number for the spectrophotometric absorbance, indicating properly that the NADH which absorbs at 340 nanometers was still present. However, for specimens with low triglyceride values, the color loss would be small; and thus in the low range the assay is liable to inaccuracy due to the type of error usually involved in a calculation dependent upon a difference of very large numbers. This difficulty would ultimately manifest itself as a lack of precision or reproducibility at low levels.

A second problem common to systems which measure the NADH system at 340 nanometers is that it is a well known fact that lipemia interferes to a much greater degree at low wavelengths such as at 340 nanometers, as opposed, for example, to measurements at 600–700 nanometers. This interference expresses itself as increased absorbance readings, further compounding the inaccuracy problems cited above.

The third common problem attendant with this type system is that the chromophore itself is comparatively insensitive, that is, each interconversion of NADH/NAD produces a small absorbance change, thus limiting the analyst in his ability to define concentration differences to the precision of his spectrophotometer; this is in contrast to use of a chromophore of high sensitivity which, given the same degree of spectrophotometric precision, expresses itself as a smaller and thus more accurately defined concentration difference.

Further as to the particular approach advocated by Bucolo and David, still another disadvantage was that their system was particularly vulnerable to a type of interference from the enzyme alkaline phosphotase, similar to that mentioned above with reference to enzymatic determination of glycerol.

The prior art method of Bucolo and David, which as noted above had disadvantages such as pointed out, uses the following reaction sequence:

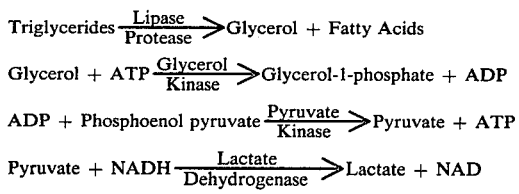

IV. The Present Invention

The present invention accomplishes a fully enzymatic assay for triglyceride without use of a protease and with the novel inclusion of iron in the reaction medium, while avoiding various disadvantages of the prior art, and of earlier prior art attempts at improvement.

For one thing, the procedure of this invention, as it is totally enzymatic, is capable of being performed rapidly and in a single tube, thus representing great advantages in that larger numbers of assays may be performed by a single technician in a reasonable time frame.

Additionally, the method of this invention is free from the more common sources of interferences in triglyceride assays, such as that usually encountered from phospholipids and glucose. Freedom from phospholipids is achieved by the use of the enzyme lipase which is highly specific for triesters of glycerol; glucose is not a source of interference, due to the mild reaction conditions employed in the assay system.

Further, the method of the present invention does not require expensive instrumentation or expensive equipment capable of measurements in the U.V. Range for accomplishment of the assay.

Moreover, the present invention, for the first time in triglycerides assays, achieves an accuracy sensitivity, and reliability, with health-improving and life-saving benefits which the prior art assays have hoped for but failed to achieve; for although prior art methods have overcome certain disadvantages of prior assays, none has been successful in avoiding other disadvantages or in accomplishing the benefits and advantages of this present invention.

At this point the present invention departs from prior art in that all reactions are carried out in the presence of iron.

The reaction of the present invention utilizes an enzymatically catalyzed hydrolysis with lipase. The glycerol thus liberated is then converted to dihydroxy acetone and NADH through the following course of reactions as suggested by several authors:[9, 10]

[9]Eggstein, M. and Kreutz, F. H., *Klin. Wochenschr.*, Vol. 44:262 (1966).
[10]Bucolo, G. and David H.: *Clin. Chem.*, 19:476 (1973), and Bucolo's U.S. Pat. No. 3,703,591.

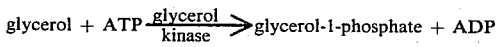

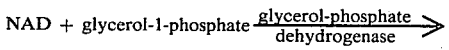

Dihydroxyacetone + NADH

Abbreviations

ATP=Adenosine Triphosphate;
ADP=Adenosine Diphosphate;
NAD=Nicotinamide Adenine Dinucleotide;
NADH=Nicotinamide Adenine Dinucleotide (reduced);

The present invention, in contrast, further departs from prior art in providing the following additional reactions:

(1) 

(2) 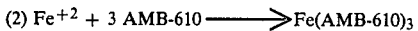

(Absorbs at 610 nm)

Abbreviations

PMS=Phenazine Methosulfate; and
AMB-610=9-(2-pyridyl)-acenaphtho[1,2-e]-as-triazine sulfonate Within the concepts of the present invention, all of these reactions may be carried out within a single reaction vessel.

The addition of the inventive steps as represented by reactions "1" and "2" above achieves the highly advantageous and very desirable effect of greatly enhancing the sensitivity of the assay, and of also lessening the interference normally encountered when lipemic specimens are assayed. This greatly increased sensitivity is due to the far greater absorptivity of the iron-chromophore complex over NADH.

The increase in sensitivity is about six-fold, in comparison to the cited Bucolo and David alternative.

As the resulting iron chromophore exhibits an absorption peak at 610 nm, the interference from lipemic specimens is greatly reduced over those methods which require measurement at lower wavelengths such as 340 nm.

This tremendous advantage, of a six-fold increase in sensitivity, as achieved here by the concept of the extra steps of reactions involving iron ions, is so great that in considering the nature and merits of the invention one helpful factor of consideration may be to look backwards and try to determine why this invention has apparently been unobvious to not only Bucolo and David but also to all others of the prior art, particularly since the medical field may be considered to be very active in many aspects of research and development with huge research budgets and with highly competitive commercial interests, and particularly also in view of the fact that the use of the redox state of iron has been known and used in the past to enhance quantitation of various analytes.

And after all, there had long been a vital need for better triglycerides assaying, and there had been various prior art procedures which did produce NADH as a reaction product, and NADH is known to be measurable.

Nevertheless, the prior art, prior to the present invention, did not conceive of this invention nor depart from the prior art procedures, with the concepts of this invention's step of an iron reduction in a reaction with NADH, and with this invention's use of an iron chromophore which advantageously gives a desired high wavelength observation and measurement.

If this type of backward-vision were attempted, it is to be noted that any step subsequent to the production of NADH, and in particular an extra step involving an iron reaction with an iron chromophore, would likely have been not only not obvious, but quite to the contrary, such a departure would have indeed been even very much contra-indicated. This is due to the long-reported and widely known fact that ferric ($Fe^{+3}$) ions exert an inhibitory effect on the catalytic action of enzymes in general, and in particular the enzyme lipase, therefore eliminating its possible use in an assay system which is lipase activated.[11] The present invention overcomes this reported inhibitory effect, thus allowing the use of a unique coupling reaction in the assay procedure.

[11]Laboureur, P. and Laborousse, M., *Bull. Soc. Chem. Biol.* 48:747 (1966).

Further in the method of Bucolo and David, which, unlike the present invention, required the presence of protease to effect complete hydrolysis, the presence of iron in their assay system was also strongly contra-indicated by the fact that it is well known that the presence of heavy metals such as iron causes irreversible inhibition of proteases in general and chymotrypsin in particular.[12]

[12]Burgmeyer, H. V., *Methods of Enzymatic Analysis*, (New York Academic Press, 1965) page 972.

With such significant contra-indications to the concepts of the present invention, even if the present invention's concepts are held up alongside Bucolo and David, which is apparently the closest prior art approach to the departures of the present invention, it is seen that the present invention's concepts are an unobvious departure from the closest prior art; and the contrast to Bucolo and David seems significant in considering the merits and benefits and nature of the present invention.

IV. A. Description of the Present Invention

In a preferred embodiment of the present invention, an aliquot of a triethanolamine buffer containing a ferrous indicator such as 9-(2-pyridyl)-acenaphtho[1,2-e]-as-triazine sulfonate, at pH 9.4, is added to a vial which contains lipase, adenosine triphosphate, glycerol-3-phosphate dehydrogenase, and glycerol kinase. A serum sample containing triglyceride is then added to the above solution, along with a solution containing an electron transfer agent (such as phenazine methosulfate), nicotinamide adenine dinucleotide (oxidized), and ferric ions.

The mixture is then incubated at a temperature of 37° C. for a period of time, and the resulting blue color representing triglyceride is then read in a spectrophotometer at a wavelength of 610 nanometers; and the resulting absorbance is recorded and is used to calculate the triglyceride content of the original sample by comparison to the absorbance of a standard solution of triglyceride which has been treated in an identical manner as the serum sample.

More specifically, examples or embodiments are now set forth:

EXAMPLE 1

There are added 2.0 milliliters of a 0.128 M triethanolamine buffer, pH 9.4, containing 9-(2-pyridyl)-acenaphtho[1,2-e]-as-triazine sulfonate, in a concentration of 1.6 mmol/L, to a lyophilized vial containing 18 μmol adenosine triphosphate, 20.5 μmol of $MgSO_4$, 660 units of liapse, 3 I.U. glycerol-3-phosphate dehydrogenase, and 0.29 I.U. of glycerol kinase, all of the above being in a lyophilized form to assure maximum stability.

To this mixture is added a 20 microliter (0.02 milliliter) sample of serum which contains triglyceride. To this mixture is then added a 1.5 milliliter aliquot of a solution containing 47 μmol/L phenazine methosulfate, 27 mmol/L nicotinamide adenine dinucleotide (oxidized), and 0.466 mmol/L ferric ions.

The resultant solution is then mixed thoroughly and incubated at a temperature of 37° C. for 20 minutes. (Upon the addition of the solution containing phenazine methosulfate, it is preferable that the solution be protected from the presence of strong light or sunlight.) Upon completion of the 20-minute incubation period, the absorbance of the mixture is then measured in a spectrophotometer at 610 nanometers against a reagent blank which is prepared in an identical manner as the serum reaction mixture, except that 20 microliters of distilled water is substituted for the serum sample.

The triglyceride content of the serum sample is then calculated by comparison of the measured absorbance to the absorbance developed by a solution of known triglyceride content which has been treated in an identical manner as the serum sample.

Under the conditions as described above, a linear response (i.e., absorbance measured varying directly with the concentration of triglyceride in the original serum sample) will be observed up to a level of approximately 500 mg/dl of triglyceride. As there is a slow but continual increase in absorbance in all tubes, including the reagent blank tube, it is recommended that the analyst re-zero the spectrophotometer with the reagent blank tube between test readings for optimum results. (One unit of lipase activity is that amount of enzyme which will liberate 1 μmol of fatty acids per minute at pH 8.9 and 25° C.).

EXAMPLE 2

In a preferred form which is more suitable for adaptation to automated instrumentation, a 7 microliter serum sample is dispensed into a reaction vessel; and to this vessel are simultaneously added a 0.5 milliliter aliquot of a reagent containing 36 mmol/L of adenosine triphosphate, 40.9 mmol/L $MgSO_4$, 1,318,000 units/L of lipase, 6,040 I.U./L of glycerol-3-phosphate dehydrogenase, and 570 I.U./L of glycerol kinase; a 1.5 ml aliquot of a reagent containing 47 μmol/L of phenazine methosulfate, 0.466 mmol/L ferric ions and 27.3 mmol of nicotinamide adenine dinucleotide (oxidized); and a 1.5 ml aliquot of a 0.17 molar triethanolamine buffer, pH 9.4, containing 2.1 mmol/L of 9-(2-pyridyl)-acenaphtho[1,2-e]-as-triazine sulfonate. The solution is then mixed and incubated at a temperature of 37° C. for approximately 15 minutes. The final absorbance of the mixture is then spectrophotometrically measured at 610 nanometers, and the amount of triglyceride in the original sample is calculated as in Example 1 above. Under these conditions a linear absorbance response has been demonstrated in serum samples containing up to 1000 mg/dl of triglyceride.

EXAMPLE 3

As in Example 1 except that 1.6 mmol/L of bathophenanthroline sulfate is substituted for the 1.6 mmol/L of 9-(2-pyridyl)-acenaphtho[1,2-e]-as-triazine sulfonate.

EXAMPLE 4

As in Example 1 except that 1.6 mmol/L of FerroZine[13] is substituted for the 1.6 mmol/L of 9-(2-pyridyl)-acenaphtho[1,2-e]-as-triazine sulfonate.

[13] FerroZine is a trademark of Hach Chemical Co., of Amex, Iowa. As stated in the Aldridge Catalog—Hanbook of Organic and Bio-chemicals, p. 385 (1977–8), its composition is:

3-(2-pyridyl)-5,6-diphenyl-1,2,4-triazine-p,p'-disulfonic acid, disodium salt trihydrate.

(Similarly to the embodiments shown by Examples 3 and 4, the other iron chelators (such as bathophenanthroline sulfonate and FerroZine[13]) may be substituted on an equimolar basis for the 9-(2-pyridyl)-acenaphthol[1,2-e]-as-triazine sulfonate set forth in Example 2.)

[13] FerroZine is a trademark of Hach Chemical Co., of Amex, Iowa. As stated in the Aldridge Catalog—Hanbook of Organic and Bio-chemicals, p. 385 (1977–8), its composition is:

3-(2-pyridyl)-5,6-diphenyl-1,2,4-triazine-p,p'-disulfonic acid, disodium salt trihydrate.

Obviously having knowledge of the aforementioned principles, one skilled in the art may make minor modifications in the assay without departing from the inventive concepts herein contained.

For example, the exact unitage of lipase may be lowered with an accompanying increase in incubation time to effect complete hydrolysis.

Similarly, the exact composition of the buffer, which has been optimized in the disclosed assay systems, may be modified slightly as to type the pH without serious effects on the assay system.

What is claimed is:

1. In a method for the determination of triglycerides in biological fluids by enzymatically hydrolyzing the triglycerides with lipase, converting the product thus formed to glycerol-1-phosphate with adenosine triphosphate (ATP) and the enzyme glycerol kinase (GK), and converting the glycerol-1-phosphate to dihydroxyacetone phosphate by the use of the enzyme glycerol phosphate dehydrogenase (GPDH) with the concomitant reduction of nicotinamide adenine dinucleotide (NAD) to the reduced form NADH, the improvement, in said triglyceride assay, of reacting the NADH thus formed with iron in the oxidized (ferric) state to form reduced (ferrous) iron, said ferric ion being included in the same reaction mixture as the lipase while the lipase is present therein and is exerting its enzymatic effect, said reaction being mediated by an electron transfer agent, and reacting the reduced iron with an iron chelator to form a chromophore of high intensity, and thereafter quantitating the amount of triglyceride present in the biological fluid by measuring the amount of chromphore formed.

2. The method of claim 1 wherein the electron transfer agent is phenazine methosulfate.

3. The method of claim 1 wherein the iron chelator is 9-(2-pyridyl)-acenaphtho[1,2-e]-as-triazine sulfonate.

4. The method of claim 1 wherein the iron chelator is bathophenanthroline sulfonate.

5. The method of claim 1 wherein the iron chelator is 3-(2-pyridyl)-5,6-diphenyl-1,2,4-triazine-p,p'-disulfonic acid, disodium salt trihydrate.

6. In a method for the determination of triglycerides in biological fluids in which the triglycerides are enzymatically hydrolyzed by use of the enzyme lipase, and by involving the products of the lipase-catalyzed reaction in a further reaction or set of reactions which ultimately yields a change in the oxidation state of an intermediate compound, the improvement of including iron, in the form of ferric ion, in same reaction mixture as the enzyme lipase, and subsequently using the change in the oxidation state of the iron as a means of quantitating the triglyceride content.

* * * * *

UNITED STATES PATENT OFFICE
CERTIFICATE OF CORRECTION

Patent No. 4,245,041    Dated January 13, 1981

Inventor(s) Jerry W. Denney

It is certified that error appears in the above-identified patent and that said Letters Patent are hereby corrected as shown below:

Column 1, line 35, after "1162," insert --1960--.
Column 2, line 62, change "compromise" to --comprise--.
Column 3, line 14, change "arount" to --around--.
Column 4, line 18, change "attition" to --addition--.
Column 8, line 24, change the letter "e" which appears within the square brackets and the contiguous letters "as" of the chemical compound to --e-- and --as--.
Column 9, lines 41 and 42, change the letter "e" which appears within the square brackets and the contiguous letters "as" of the chemical compound to --e-- and --as--.
Column 9, line 65, change the letter "e" which appears within the square brackets and the contiguous letters "as" of the chemical compound to --e-- and --as--.
Column 9, last line, change "liapse" to --lipase--.
Column 10, line 55, change the letter "e" which appears within the square brackets and the contiguous letters "as" of the chemical compound to --e-- and --as--.
Column 10, last line, change the letter "e" which appears within the square brackets and the contiguous letters "as" of the chemical compound to --e-- and --as--.
Column 11, line 5, change the letter "e" which appears within the square brackets and the contiguous letters "as" of the chemical compound to --e-- and --as--.
Column 11, line 14, change the letter "e" which appears within the square brackets and the contiguous letters "as" of the chemical compound to --e-- and --as--.

UNITED STATES PATENT OFFICE
CERTIFICATE OF CORRECTION

Patent No. 4,245,041  Dated January 13, 1981

Inventor(s) Jerry W. Denney

It is certified that error appears in the above-identified patent and that said Letters Patent are hereby corrected as shown below:

Column 11, line 14, before the square brackets, the letters "thol" should be only the letters --tho--.
Column 11, line 28, before the "pH", change the word "the" to the word --and--.
Column 12, line 15, being the last line of Claim 1, change "chromphore" to --chromophore--.
Column 12, line 20, being line 2 of Claim 3, change the letter "e" which appears within the square brackets and the contiguous letters "as" of the chemical compound to --e-- and --as--.
Column 11, line 7, change "Hanbook" to --Handbook--.
Column 11, line 16, change "Hanbook" to --Handbook--.

Signed and Sealed this

Twenty-sixth Day of May 1981

[SEAL]

Attest:

Attesting Officer

RENE D. TEGTMEYER

Acting Commissioner of Patents and Trademarks